(12) United States Patent
Weng

(10) Patent No.: US 8,424,369 B2
(45) Date of Patent: Apr. 23, 2013

(54) SURFACE TENSION MEASURING DEVICE AND METHOD THEREOF

(75) Inventor: Huei-Chu Weng, Taoyuan County (TW)

(73) Assignee: Chung Yuan Christian University, Chung Li (TW)

( * ) Notice: Subject to any disclaimer, the term of this patent is extended or adjusted under 35 U.S.C. 154(b) by 355 days.

(21) Appl. No.: 12/944,096

(22) Filed: Nov. 11, 2010

(65) Prior Publication Data

US 2011/0197663 A1    Aug. 18, 2011

(30) Foreign Application Priority Data

Feb. 12, 2010 (TW) .............................. 99104603 A

(51) Int. Cl.
*G01N 13/00* (2006.01)

(52) U.S. Cl.
USPC ........................................ 73/64.52; 73/64.51

(58) Field of Classification Search ............... 73/64.48, 73/64.51, 64.52
See application file for complete search history.

(56) References Cited

U.S. PATENT DOCUMENTS

2003/0205079 A1* 11/2003 Taylor ........................... 73/64.48
2004/0177680 A1*  9/2004 Skogo et al. .................. 73/64.51

* cited by examiner

*Primary Examiner* — Hezron E Williams
*Assistant Examiner* — Nathaniel Kolb
(74) *Attorney, Agent, or Firm* — Rosenberg, Klein & Lee

(57) ABSTRACT

A surface tension measuring device and a method thereof are revealed. The surface tension measuring device includes a container and a hole. A liquid analyte is filled into the container and the hole is disposed on a wall surface of the container while the liquid analyte forms a drop on the hole. The surface tension of the liquid analyte is correlated with an internal gas pressure inside the container, an external gas pressure outside the container and a level of the liquid analyte. Thus the surface tension of the liquid analyte is obtained by control of the increasing of the liquid analyte level or pressure difference inside and outside the container. Therefore, the reduction of measuring time, less space occupied, lower equipment cost and reduced operation complexity are achieved.

8 Claims, 5 Drawing Sheets

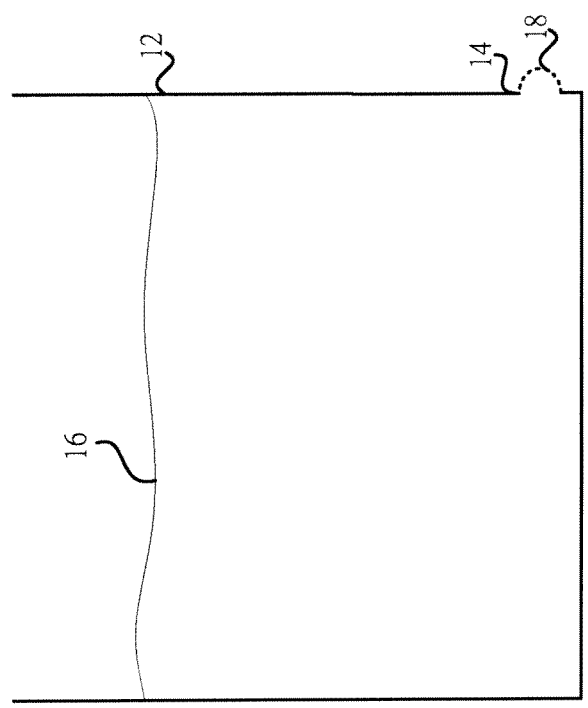

SURFACE TENSION MEASURING DEVICE AND METHOD THEREOF

BACKGROUND OF THE INVENTION

1. Field of Invention

The present invention relates to a measuring device, especially to a surface tension measuring device and a method thereof.

2. Description of Related Art

Surface tension is caused by cohesion of material molecules. Several effects of surface tension can be seen in our daily lives. For example, rise or fall of liquid in a capillary tube, beading of water, and a fountain pen in which surface tension keeps the ink on a nib and not dropped due to gravity. There is also a plurality of applications of surface tension effect in industrial techniques such as fluid seal, spin coating, printer ink jetting, surface wetting, etc.

The surface tension effects and applications are pervasive in many areas so that the surface tension measurement plays an important role on industrial and research institutes. Most of surface tension measuring techniques available now use contact angle measuring instruments. The instrument includes a machine, a prime lens, a camera, a back light module, a computer and algorithm package software. The measured value of the contact angle, estimated value of gas-liquid surface tension and calculated value of gas-solid surface tension are substituted into a force balance equation of the droplet interface so as to determine solid-liquid surface tension (or abbreviated as surface tension). However, such measuring method has disadvantages of long measuring time, large space occupation, high instrument cost and high operation complexity.

Refer to Taiwanese Pat. No. 200928343, a surface tension measuring technique is revealed. A container with a liquid analyte and a vertical tube are connected by U-shaped tube sets. An outlet of the vertical tube is located at the same level of the container. Then fill a liquid analyte into the container. When a hemispherical drop is formed on the outlet of the vertical tube, measure the level difference between the liquid level in the container and the liquid level in the vertical tube. In case the effect of gravity on the drop shape is negligible, the measured results obtained are substituted into an equation derived from the force balance relations so as to get the surface tension of the liquid analyte. However, there are a plurality of factors that affect the precision of measurement such as the tube length, the location of the tube (outlet), and the effect of gravity on the drop. Thus the measurement errors increase, combined with other disadvantages such as large space occupied, high instrument cost and high operation complexity.

Like many other common physical phenomena, how surface tension occurs and the measurement of surface tension play important roles in the scientific education. Yet most of surface tension measuring instruments available now are with defects of high cost, inconvenience in carrying and considerable complexity in measuring and they are unable to be applied in our daily lives or teaching.

Thus there is a need to provide a surface tension measuring instrument and a method thereof that reduce the measuring time, the space occupied, the equipment cost, the operation complexity and overcomes the above shortcomings.

SUMMARY OF THE INVENTION

Therefore it is a primary object of the present invention to provide a surface tension measuring device and a method thereof in which surface tension is measured by liquid analyte that forms a drop on the hole so as to reduce measuring time, the space required, the equipment cost and the operation complexity.

In order to achieve above object, a surface tension measuring device and a method thereof according to the present invention consist of a container and a hole. A liquid analyte is filled into the container and the hole is disposed on a wall surface of the container. While the liquid analyte forming a drop on the hole, the surface tension of the liquid analyte is correlated with gas pressures inside and outside the container, and the level of the liquid analyte.

Moreover, the surface tension measuring device further includes scales disposed on a side wall of the container so as to measure the increasing of the liquid analyte level in the container.

Furthermore, the surface tension measuring device further consists of a drop detector, a water gauge, at least one pressure gauge and a microprocessor. The drop detector detects shape of the drop formed on the hole, the water gauge measures the level of the liquid analyte in the container, and the pressure gauge checks the gas pressures inside and outside the container. According to measured results of the level of the liquid analyte and the gas pressures inside and outside the container, the microprocessor gets the surface tension of the liquid analyte.

BRIEF DESCRIPTION OF THE DRAWINGS

The structure and the technical means adopted by the present invention to achieve the above and other objects can be best understood by referring to the following detailed description of the preferred embodiments and the accompanying drawings, wherein

FIG. 4 is a further embodiment of a surface tension measuring device according to the present invention.

DETAILED DESCRIPTION OF THE PREFERRED EMBODIMENT

Figure 1A:
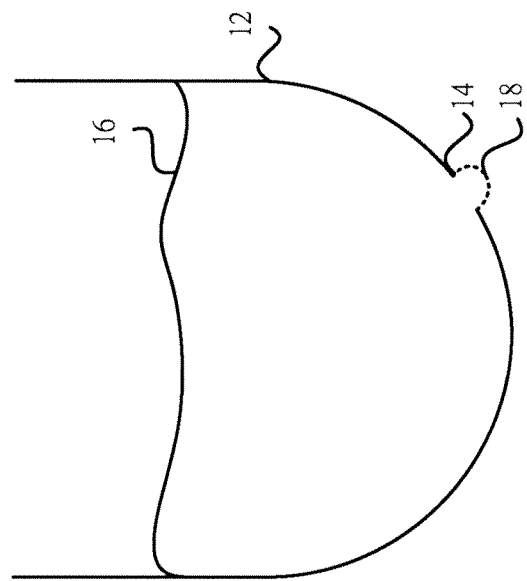
FIG. 1A is a schematic drawing showing an embodiment of a surface tension measuring device according to the present invention.
Figure 1B:
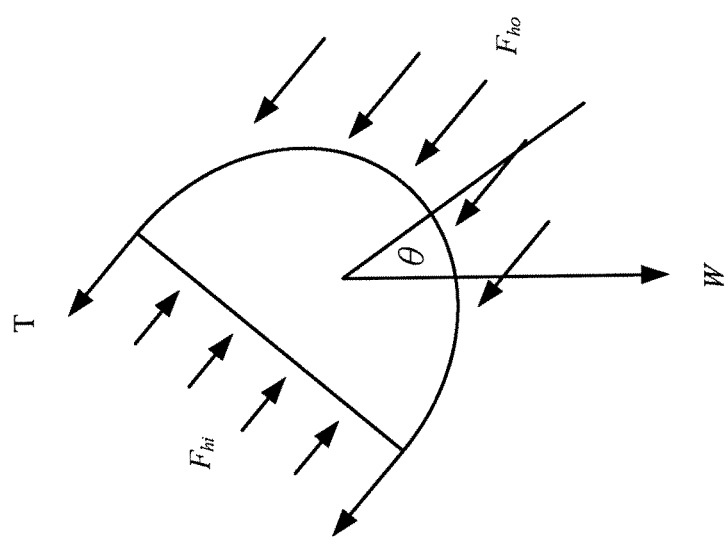
FIG. 1B is a schematic drawing showing forces acted on a drop according to the present invention.

Refer to FIG. 1A and FIG. 1B, a surface tension measuring device of the present invention includes a container 12 and a hole 14. Liquid analyte 16 is put into the container 12 with the hole 14. The hole 14 is arranged on a wall surface of the container 12. When the liquid analyte 16 is added into the container 12 continually, a drop 18 is slowly formed on the hole 14. By control of the level of the liquid analyte 16 in the container 12, the liquid analyte 16 forms a hemispherical drop on an opening of the hole 14. Thus the increasing of the liquid analyte 16 level in the container 12 determines surface tension of the liquid analyte 16. Therefore, the measuring time is reduced, so is the space required, the equipment cost and the operation complexity. In a preferred embodiment, the shape of the drop 18 on the surface tension measuring device is hemispherical. The present invention can also fix the level of the liquid analyte 16 in the container 12 and change the pressure difference inside and outside the container 12 to measure the surface tension of the drop formed.

Refer to FIG. 1A, the container 12 is to receive the liquid analyte 16 and is arranged with the hole 14. Once the level of the liquid analyte 16 is a bit higher than the opening of the hole 14, the drop 18 is formed on the opening of the hole 14 by the liquid analyte 16. Keep controlling the increasing of the liquid analyte 16 level or the pressure difference inside and outside the container 12 so as to make the drop 18 become hemispherical. As shown in FIG. 1B, in the drop 18, the position at an angle θ from a vertical direction is with maximum surface tension. Now any increasing in liquid pressure inside the drop 18 will push the liquid out of the hole 14 (yet the drop 18 may be not separated from the hole 14 completely). Then measure gas pressures inside and outside the container 12 (an internal gas pressure and an external gas pressure, respectively) and the level of the liquid analyte 16 in the container so as to obtain the surface tension.

Still refer to FIG. 1B, as shown in figure. Forces acting on the position of the drop 18 at an angle θ from the vertical direction consist of: internal liquid pressure $F_{hi}=p_i(\pi R^2)$, external gas pressure $F_{ho}=p_{out}(\pi R^2)$, gravity $W \cos\theta = \gamma(2\pi R^3/3)\cos\theta$, and surface tension $T=\sigma(2\pi R)$, where R is the diameter of the round hole, γ is the specific weight of liquid, $p_{out}$ is the external gas pressure, $p_i$ is the internal gas pressure, σ is the surface tension. Because the value of R is too small, the internal liquid pressure value $p_i$ is considered as a constant—$\gamma h+p_{in}$, wherein $p_{in}$ is internal gas pressure. The following equation is derived from the balance of the forces acted on the drop 18($T+F_{ho}=F_{hi}+W \cos\theta$):

$$\sigma = \frac{(\gamma h + (p_{in} - p_{out}))R}{2} + \frac{\gamma R^2 \cos\theta}{3} \quad (1)$$

Measure the increasing of the liquid analyte level h at this moment (if the value of ($p_{in}-p_{out}$) is already known) or the pressure difference inside and outside the container 12 $p_{in}-p_{out}$ (if the value of h is already known) and substitute the value obtained into the equation so as to determine the surface tension of the liquid analyte 16.

The derivation of the equation (1) is based on the force balance of the drop 18 in the direction perpendicular to the wall surface under the gravitational field. Thus the precision of results is not affected by the contact angle measurement (measuring the angle between the direction of surface tension and the vertical direction of the wall surface) and the gravity of the drop 18. Moreover, the hole is on the wall surface so that there is no precision problem like the location of the capillary tube. The device is not including a capillary tube so that the length of the capillary tube will not affect the measuring precision. Furthermore, the capillarity action is inversely proportional to the surface area of the liquid analyte 16. Thus the larger surface area the liquid analyte has 16, the smaller the capillarity action and the higher the measuring precision. And it is learned from the equation (1) that the level and the pressure difference is inversely proportional to the diameter of the hole 14. Thus the smaller the diameter of the hole 14, the larger value of the level and the pressure difference obtained. That means the higher the measuring precision is.

Figure 2:
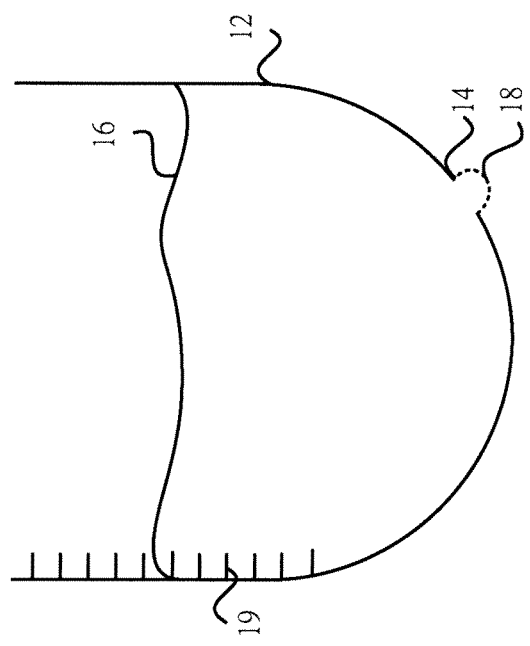
FIG. 2 is another embodiment of a surface tension measuring device according to the present invention.

Refer to FIG. 2, another embodiment is revealed. As shown in figure, the surface tension measuring device of the present invention further includes scales 19 arranged at one side of the container 12 so as to measure the increasing of the liquid analyte 16 level in the container 12. Due to the scales 19, the increased height of the liquid analyte 16 in the container 12 is checked and obtained easily. Thus the equipment cost is down and the operation complexity is reduced.

Figure 3:
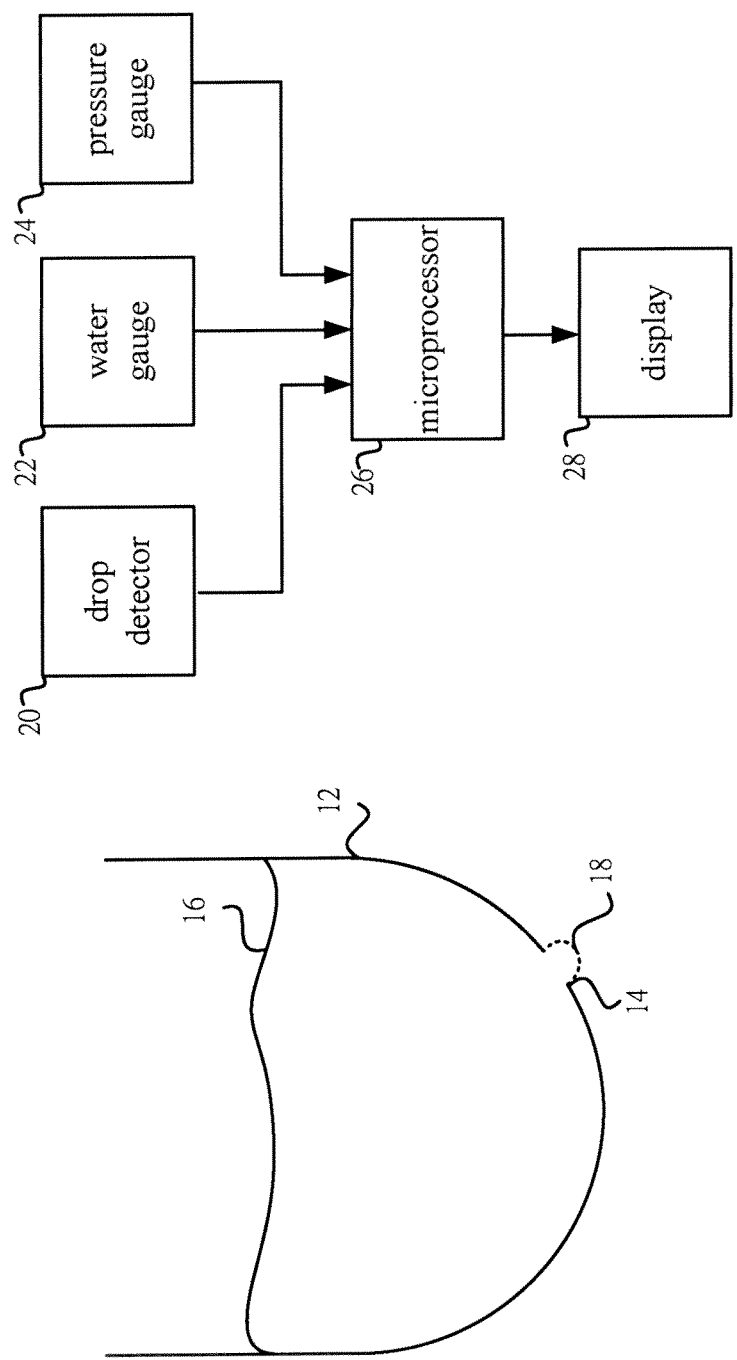
FIG. 3 is a further embodiment of a surface tension measuring device according to the present invention.

Refer to FIG. 3, a further embodiment of the surface tension measuring device is disclosed. The difference between this embodiment and above one is in that this embodiment further consists of a drop detector 20, a water gauge 22, at least one pressure gauge 24 and a microprocessor 26. The drop detector 20 detects the size of the drop 18 formed on the hole 14 of the container 12 and the water gauge 22 measures the level of the liquid analyte 16 in the container 12. As to the pressure gauge 24, it checks the gas pressures inside and outside the container 12. When the drop detector 20 detects that the drop 18 is a hemisphere, the water gauge 22 starts measuring the level of the liquid analyte 16 in the container 12. At the same time, the pressure gauge 24 checks the gas pressures inside and outside the container 12. The measured results of the liquid level and the pressures are sent to the microprocessor 26 so as to obtain the surface tension of the drop 18 and data of the surface tension is shown on a display 28.

Refer to FIG. 4, a further embodiment is revealed. As shown in figure, the difference between this embodiment and the embodiment in FIG. 1 is in that the container 12 of this embodiment is a cube. The shape of the container 12 is not restricted to a specific shape. The container 12 is arranged with the hole 14, and the drop 18 formed on the surface of the hole 14 is detected and measured.

In summary, a surface tension measuring device and a method thereof consist of a container and a hole. A liquid analyte is filled into the container and the hole is arranged on a wall surface of the container so that the liquid analyte forms a drop on the hole. Based on the principle that surface tension of the liquid analyte is correlated with gas pressures inside and outside the container as well as the level of the liquid in the container, the surface tension of the drop is measured. Thus the measuring time, the space occupied, the equipment cost, the measurement errors and the operation complexity are all reduced. Moreover, users can get the surface tension of the liquid analyte by easy operation.

Additional advantages and modifications will readily occur to those skilled in the art. Therefore, the invention in its broader aspects is not limited to the specific details, and representative devices shown and described herein. Accordingly, various modifications may be made without departing from the spirit or scope of the general inventive concept as defined by the appended claims and their equivalents.

What is claimed is:

1. A surface tension measuring device comprising:
    a container filled with a liquid analyte:
    a hole disposed on a wall surface of the container and the liquid analyte forms a drop on the hole;
    means for measuring the internal and external gas pressure; and
    means for measuring the liquid level in the container.

2. The device as claimed in claim 1, wherein the container includes scales arranged at a side wall of the container so as to measure the level of the liquid analyte in the container.

3. The device as claimed in claim 1, wherein the drop is a hemisphere.

4. The device as claimed in claim 1, wherein the surface tension measuring device includes:
    a drop detector that detects shape of the drop formed on the hole;
    a water gauge that measures the level of the liquid analyte in the container;

at least one pressure gauge that checks the internal gas pressure and the external gas pressure respectively inside and outside the container; and a microprocessor which calculates the surface tension of the liquid analyte according to measured results of the level of the liquid analyte, and the internal and external gas pressure.

5. A surface tension measuring method comprising the steps of:

providing a container whose wall surface is disposed with a hole;

filling a liquid analyte into the container and the liquid analyte forms a drop on the hole;

measuring the gas pressure inside and outside the container;

measuring the level of the liquid analyte in the container;

calculating surface tension of the liquid analyte based upon the gas pressure inside and outside the container, and the level of the liquid analyte in the container.

6. The method as claimed in claim 5, wherein the step of calculating surface tension of the liquid analyte includes accounting for gravitational force acting on the drop.

7. The method as claimed in claim 5, wherein the drop is a hemisphere.

8. The method as claimed in claim 5, including a step of: detecting the shape of the drop on the hole.

* * * * *